(12) United States Patent
Maeda

(10) Patent No.: US 9,483,114 B2
(45) Date of Patent: Nov. 1, 2016

(54) MEDICAL SYSTEM

(71) Applicant: OLYMPUS CORPORATION, Hachioji-shi, Tokyo (JP)

(72) Inventor: Yorito Maeda, Kiyose (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/171,249

(22) Filed: Jun. 2, 2016

(65) Prior Publication Data

US 2016/0274661 A1    Sep. 22, 2016

Related U.S. Application Data

(63) Continuation of application No. PCT/JP2015/057859, filed on Mar. 17, 2015.

(30) Foreign Application Priority Data

Jul. 22, 2014   (JP) ................... 2014-149009

(51) Int. Cl.
*G06F 3/01* (2006.01)
*G06T 11/60* (2006.01)

(52) U.S. Cl.
CPC ............. *G06F 3/013* (2013.01); *G06T 11/60* (2013.01)

(58) Field of Classification Search
CPC .. G09G 3/3413; G09G 3/342; G09G 3/3648; G09G 2300/0452; G09G 2320/0242; G09G 2330/021; G09G 3/2074; G09G 3/2003; G02B 2027/0187; G06K 9/00597; A61B 2017/00216; A61B 5/0066; A61B 1/00009
See application file for complete search history.

(56) References Cited

U.S. PATENT DOCUMENTS

2013/0176208 A1    7/2013  Tanaka et al.
2014/0043229 A1*   2/2014  Higaki ................... G06F 3/013
                                                 345/156

FOREIGN PATENT DOCUMENTS

| JP | H09-212082 | 8/1997 |
|----|------------|--------|
| JP | H10-85172 A | 4/1998 |
| JP | H10-290392 A | 10/1998 |
| JP | 2001-299691 A | 10/2001 |
| JP | 2009-279193 A | 12/2009 |
| JP | 2013-140540 | 7/2013 |

OTHER PUBLICATIONS

Jun. 2, 2015 International Search Report issued in International Patent Application No. PCT/JP2015/057859.

(Continued)

*Primary Examiner* — Abbas Abdulselam
(74) *Attorney, Agent, or Firm* — Oliff PLC

(57) ABSTRACT

A medical system has peripheral apparatuses, a sight line operation screen in which a command area for instructing operation of the peripheral apparatuses is displayed, a sight line measuring apparatus configured to detect sight line position coordinates of an operator, a sight line recognition level calculation section configured to calculate an extent of sight line recognition by the sight line measuring apparatus, and a sight line recognition level display area configured to display a calculation result of the sight line recognition level calculation section on the sight line operation screen.

10 Claims, 8 Drawing Sheets

(56) References Cited

OTHER PUBLICATIONS

Dec. 22, 2015 Office Action issued in Japanese Patent Application No. 2015-552931.

Mar. 22, 2016 Decision to Grant a Patent issued in Japanese Patent Application No. 2015-552931.

* cited by examiner

FIG. 6

| EYEBALL MEASUREMENT STATE | DISPLAY CONTENT |
|---|---|
| BOTH EYES ARE MEASURED | 👁 👁 |
| ONLY RIGHT EYE IS MEASURED | ‿ 👁 |
| ONLY LEFT EYE IS MEASURED | 👁 ‿ |
| BOTH EYES CANNOT BE MEASURED | ‿ ‿ |

FIG.8
| TIME PERIOD [s] | 0 | 0.5 | 0.67 | 0.83 | 1 | 1.17 |
|---|---|---|---|---|---|---|
| DISPLAY |  |  |  |  |  |  |
| TIME PERIOD [s] | 1.33 | 1.5 | 1.67 | 1.83 | 2 |
|---|---|---|---|---|---|
| DISPLAY |  |  |  |  |  |

MEDICAL SYSTEM

CROSS REFERENCE TO RELATED APPLICATION

This application is a continuation application of PCT/JP2015/057859 filed on Mar. 17, 2015 and claims benefit of Japanese Application No. 2014-149009 filed in Japan on Jul. 22, 2014, the entire contents of which are incorporated herein by this reference.

BACKGROUND OF INVENTION

1. Field of the Invention

An embodiment of the present invention relates to a medical system, and particularly relates to a medical system that controls apparatuses by sight line recognition.

2. Description of the Related Art

In recent years, abundant kinds of medical apparatuses have been developed with technological advances, and the functions of the medical apparatuses have been enriched. Further, in an operating room, besides the medical apparatuses, various apparatuses such as room lights, various display apparatuses, an endoscope that picks up medical images, and a recording apparatus are disposed. A medical system has also been developed that performs centralized control and administration of various medical apparatuses including the above apparatuses with a centralized control apparatus (a system controller).

In a centralized control apparatus of a medical system of this kind, parameters or the like of controlled apparatuses are generally set and changed by an operation panel that receives a touch signal. However, operation panels are often placed in racks or carts that are installed in unsanitary regions, and surgeons cannot directly operate the operation panels in many cases. Consequently, a method is used, which gives an instruction to a nurse or the like who always stays in an unsanitary region, and causes the nurse to operate an operation panel in place of a surgeon, but there have been the problems that much time is required until the instruction is transmitted, and an operation mistake due to erroneous transmission and erroneous recognition of an instruction occurs.

Therefore, medical systems are proposed, which detect sight lines of surgeons by using head-mount displays with cameras or the like, issue commands when the sight lines stop on the operation switches of the target apparatuses for fixed time periods, and perform operations of the target apparatuses (refer to Japanese Patent Application Laid-Open Publication No. 2009-279193, and Japanese Patent Application Laid-Open Publication No. 2001-299691, for example).

SUMMARY OF THE INVENTION

A medical system of one aspect of the present invention has a plurality of controlled apparatuses; a display section in which an operation instruction region for instructing operation of the controlled apparatuses is displayed; a sight line detection section configured to detect sight line position coordinates of an operator who performs operation of the controlled apparatuses via the display section; a sight line measurement level calculation section configured to calculate an index showing reliability of the sight line position coordinates which are detected by the sight line detection section; and a sight line recognition level calculation section configured to calculate an extent of sight line recognition of the operator from a calculation result of the sight line measurement level calculation section, wherein the sight line recognition level calculation section has an eyeball measurement level determination section configured to determine whether or not the respective sight line position coordinates of a left eye and a right eye of the operator are detected in the sight line detection section, independently respectively.

BRIEF DESCRIPTION OF THE DRAWINGS

FIG. 5 is a view explaining an example of a sight line operation screen 3a;

FIG. 6 is a diagram showing an example of a display content of an eyeball recognition situation display area 33;

FIG. 8 is a view for explaining an example of timer display shown in a selected command area.

DETAILED DESCRIPTION OF THE PREFERRED EMBODIMENT(S)

Hereinafter, an embodiment will be described with reference to the drawings.

Figure 1:
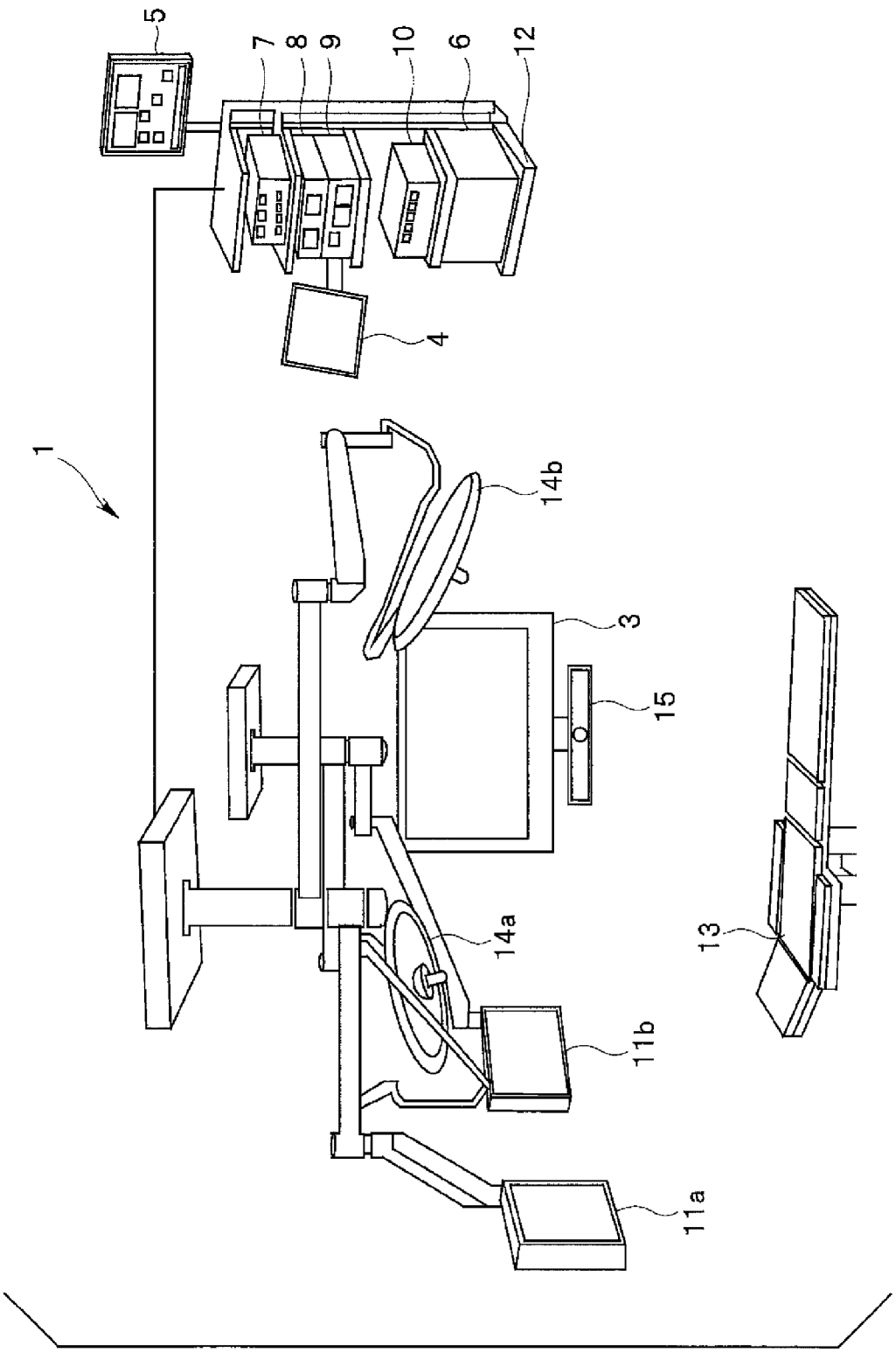
FIG. 1 is a view explaining an example of an entire configuration of a medical system 1 according to an embodiment of the present invention.

FIG. 1 is a view explaining an example of an entire configuration of a medical system 1 according to the embodiment of the present invention. As shown in FIG. 1, the medical system 1 of the present embodiment includes peripheral apparatuses 2 that are controlled apparatuses configured by a plurality of medical apparatuses, a monitor 3 configured to receive a sight line operation by an operator such as a surgeon, a sight line measuring apparatus 15 configured to recognize sight lines of the operator who performs a sight line operation by the monitor 3 and measure sight line coordinates or the like, an operation panel 4 configured to receive an operation by an operator such as a nurse, a display panel 5, and a system controller 6 configured to perform centralized control of the peripheral apparatuses 2 and the like.

The peripheral apparatuses 2 are configured by a plurality of medical apparatuses that perform observation, inspection, treatment and the like. More specifically, the peripheral apparatuses 2 are configured by an endoscope camera apparatus 7, an insufflation apparatus 8, a light source apparatus 9, an electric knife apparatus 10, monitors (a monitor 11a, a monitor 11b) and the like. Note that the peripheral apparatuses 2 are not limited to the above medical apparatuses, but may include a video tape recorder (VTR), for example.

Figure 2:
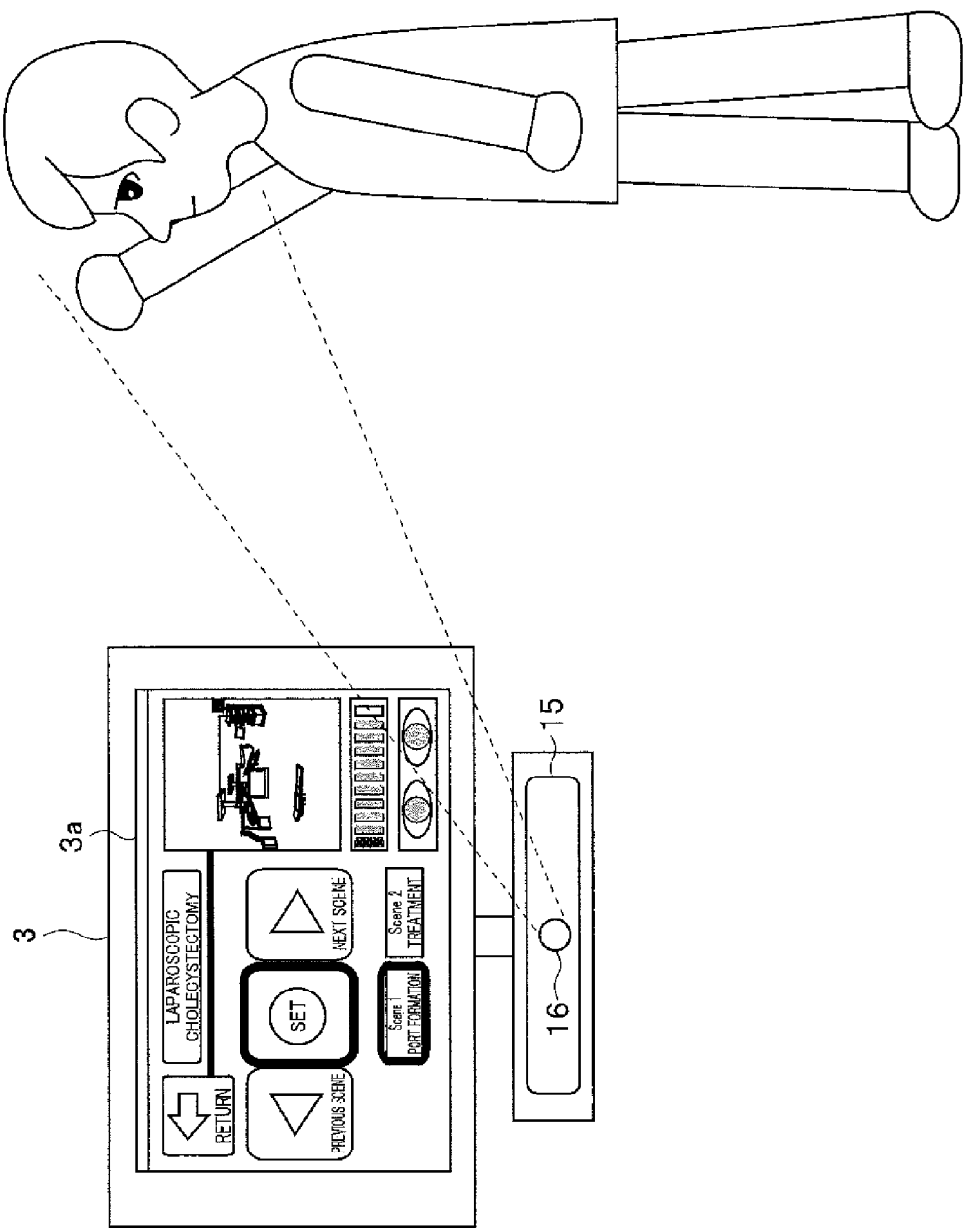
FIG. 2 is a view explaining an installation position of a sight line measuring apparatus 15.

A sight line operation screen 3a that is a display section for performing a collective operation of the peripheral apparatuses 2 is displayed on a liquid crystal display, for example, in the monitor 3. As shown in FIG. 2, for example, the sight line measuring apparatus 15 as a sight line detection section is installed at a lower portion of the monitor 3, and sight line position coordinates of a surgeon or the like are measured by the sight line measuring apparatus 15. FIG. 2 is a view explaining an installation position of the sight line measuring apparatus 15. The sight line measuring apparatus 15 includes a compact camera 16 configured to photograph eyeballs from a front direction, or the like, and measures position coordinates which the sight lines of the surgeon capture, on the sight line operation screen 3a in real time by tracking positions of pupils of the eyeballs of the surgeon. Information such as sight line position coordinates measured by the sight line measuring apparatus 15 is inputted to the system controller 6.

The operation panel 4 is a touch panel display that is configured by, for example, a liquid crystal display and a touch panel sensor which is disposed by being laid on the liquid crystal display, being integrated. The operation panel 4 is an operation apparatus for a nurse or the like staying in an unsterilized region to perform the peripheral apparatuses 2, and operation information is inputted to the system controller 6. The display panel 5 is display means capable of selectively displaying all data in a surgical operation.

The light source apparatus 9 is connected to an endoscope (not illustrated) via a light guide cable that transmits an illuminating light. The illuminating light from the light source apparatus 9 is supplied to the endoscope, and illuminates an affected part or the like in an abdominal region of a patient in which an insertion portion of the endoscope is inserted.

A camera head including an image pickup device is fitted to a proximal end side of the insertion portion of the endoscope, and an optical image of an affected part or the like is picked up with the image pickup device in the camera head. An image pickup signal picked up by the image pickup device is transmitted to the endoscope camera apparatus 7 via a cable.

The endoscope camera apparatus 7 applies predetermined signal processing to the transmitted image pickup signal, and generates a video signal. Subsequently, the endoscope camera apparatus 7 outputs the generated video signal to the monitor 11a and the monitor 11b via the system controller 6. The inputted video signal, that is, an endoscope image of an affected part or the like is displayed on the monitors 11a and 11b which are suspended from a ceiling.

A carbon dioxide cylinder not illustrated is connected to the insufflation apparatus 8, so that carbon dioxide is supplied into the abdominal region of a patient through an insufflation tube that extends to the patient from the insufflation apparatus 8.

The operation panel 4, the display panel 5, the system controller 6, the endoscope camera apparatus 7, the insufflation apparatus 8, the light source apparatus 9 and the electric knife apparatus 10 are installed on a rack 12. The system controller 6 also controls equipment that is permanently provided in the operation room such as a patient bed 13 on which the patient lies, and astral lamps (an astral lamp 14a, an astral lamp 14b) that are suspended from the ceiling, as the controlled apparatuses, besides the aforementioned peripheral apparatuses 2.

Note that FIG. 1 illustrates the medical system 1 which is provided in the operation room where an endoscopic surgical operation is performed, but a use purpose of the medical system 1 is not limited to an endoscopic surgical operation, but may be used for other operations and medical examinations. Further, the medical system 1 may be provided in a place other than an operation room, such as a consultation room. The medical system 1 may further include various kinds of apparatuses and equipment not illustrated in FIG. 1. For example, the medical system 1 may include an operating field camera that observes an operating field and the like, and the operating field camera and the like may be controlled by the system controller 6.

Figure 3:
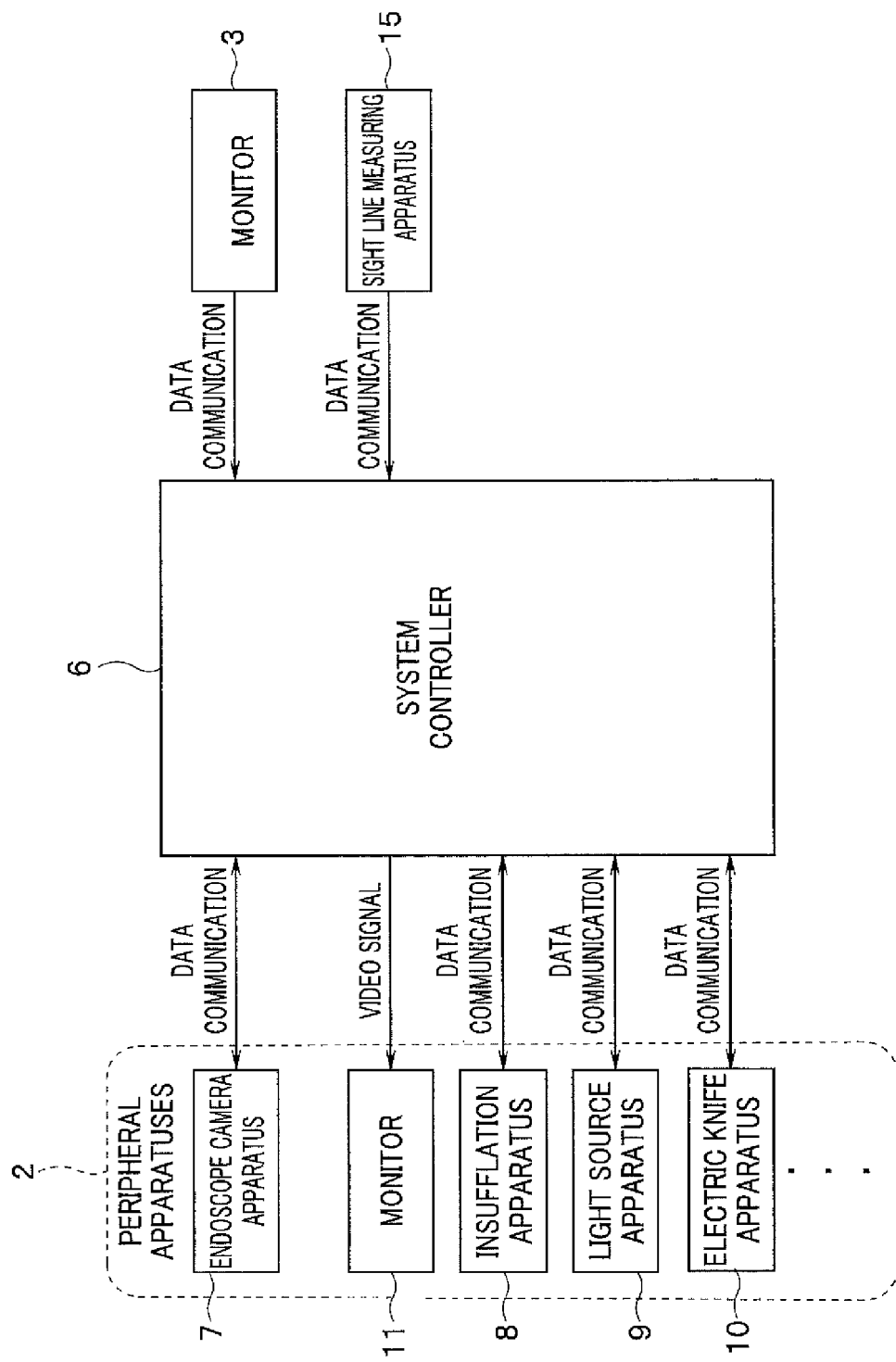
FIG. 3 is a diagram explaining a configuration of apparatuses that are connected to a system controller 6.

Next, relations between the system controller 6 and the apparatuses which are connected to the system controller 6 will be described. FIG. 3 is a diagram explaining configurations of the apparatuses which are connected to the system controller 6. As shown in FIG. 3, the peripheral apparatuses 2 that are the controlled apparatuses, the monitor 3 which is the input apparatus of an operation and the sight line measuring apparatus 15 are connected to the system controller 6. Note that as shown in FIG. 1, the operation panel 4 for a nurse or the like to perform operations of the peripheral apparatuses 2, and the display panel 5 for causing operation data and the like to be displayed are connected to the system controller 6, but since in the following, a case of controlling the peripheral apparatuses 2 by using a sight line operation will be described, and therefore, illustration is omitted in FIG. 3.

Sight line measurement information of a surgeon or the like who performs operations of the peripheral apparatuses by sight line operations is inputted to the system controller 6 from the sight line measuring apparatus 15. The inputted sight line measurement information is used in control of the peripheral apparatuses 2, or displayed on the monitor 3. Further, the sight line operation screen 3a which is generated by the system controller 6 is displayed on the monitor 3.

Set parameters of the controlled apparatuses such as the endoscope camera apparatus 7, the insufflation apparatus 8, the light source apparatus 9 and the electric knife apparatus 10 are inputted to the system controller 6. Further, new set parameters are outputted from the system controller 6 to the apparatuses in accordance with sight line operation contents that are inputted from the monitor 3. Further, a video signal that is obtained by an optical image of an affected part or the like in a body cavity of a patient being processed is inputted to the system controller 6 from the endoscope camera apparatus 7. The system controller 6 outputs the inputted video signal to the monitor 11a and the monitor 11b.

Figure 4:
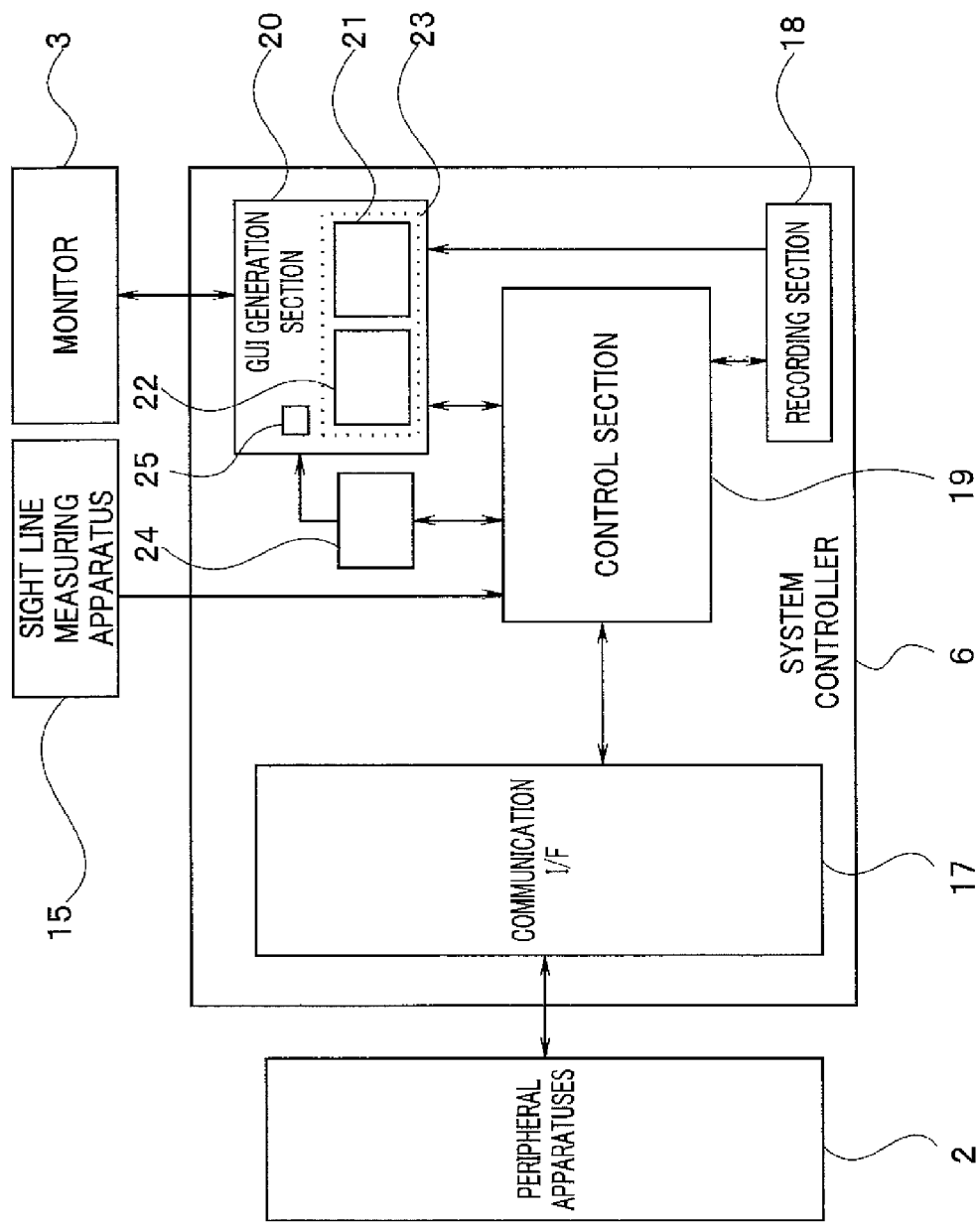
FIG. 4 is a diagram explaining a detailed configuration of the system controller 6.

A detailed configuration of the system controller 6 which is connected to the other apparatuses in this way will be described with use of FIG. 4. FIG. 4 is a diagram explaining the detailed configuration of the system controller 6. As shown in FIG. 4, the system controller 6 includes a communication interface (hereinafter, referred to as communication I/F) 17 configured to perform communication with the peripheral apparatuses 2 which are controlled apparatuses, a recording section 18 in which various parameters and the like are stored, a control section 19 configured to control an operation of the entire system controller 6, a GUI generation section 20 configured to generate the sight line operation screen 3a which is displayed on the monitor 3, and a measurement section 24 configured to perform measurement of time.

The communication I/F 17 receives various data and set parameters from the peripheral apparatuses 2 which are connected to the system controller 6 and are enabled to be subjected to centralized control, inputs the data, the parameters and the like to the control section 19, and outputs signals that are generated in the control section 19 to operate the peripheral apparatuses 2 to the peripheral apparatuses 2.

Various data, parameters and the like which are necessary to execute a program for operating the system controller 6 and other programs, for example, are stored in the recording section 18.

Various data, set parameters and the like are inputted to the control section 19 from the peripheral apparatuses 2 via the communication I/F 17. Further, the sight line measurement information of a person who performs a sight line operation such as a surgeon is inputted from the sight line measuring apparatus 15. The control section 19 reads a program, various data, parameters and the like from the recording section 18 and executes the program. The control section outputs the sight line measurement information and other necessary data to the GUI generation section 20, and performs control to generate the sight line operation screen 3*a*. Further, the control section 19 generates set parameters for controlling the peripheral apparatuses 2 on the basis of the data inputted from the GUI generation section 20 and the sight line measurement information, and outputs the set parameters to the peripheral apparatuses 2 via the communication I/F 17.

The GUI generation section 20 has a sight line recognition level calculation section 23 configured by a sight line measurement level calculation section 21 and an eyeball measurement level determination section 22.

The sight line measurement level calculation section 21 calculates an index indicating to what extent the sight line of a surgeon is reliably measured on the basis of the sight line measurement information or the like that is inputted from the sight line measuring apparatus 15. When a value of a measurement level is outputted from the sight line measuring apparatus 15, the value may be directly used as the index, or the value converted into percentage may be used. Further, the index may be calculated with a unique method of considering an element that affects sight line measurement, by measuring a distance between the sight line measuring apparatus 15 and the surgeon, and calculating the index from a difference from an optimal distance for sight line measurement, for example. Note that when the index is calculated from the distance between the sight line measuring apparatus 15 and the surgeon, a distance sensor that measures a distance between predetermined sites by perceiving movement of a moving body, such as a distance image sensor, can be used.

The eyeball measurement level determination section 22 determines whether or not sight line coordinates are measured, with respect to each of a right eye and a left eye of the surgeon, on the basis of the sight line measurement information which is inputted from the sight line measuring apparatus 15.

Further, the GUI generation section 20 generates the sight line operation screen 3*a* which is displayed on the monitor 3 by using the index which is calculated in the sight line measurement level calculation section 21, the determination result of the eyeball measurement level determination section 22, and various data, parameters and the like which are inputted from the control section 19 and the recording section 18, in accordance with an instruction from the control section 19. The generated sight line operation screen 3*a* is outputted to and displayed on the monitor 3.

Figure 5:
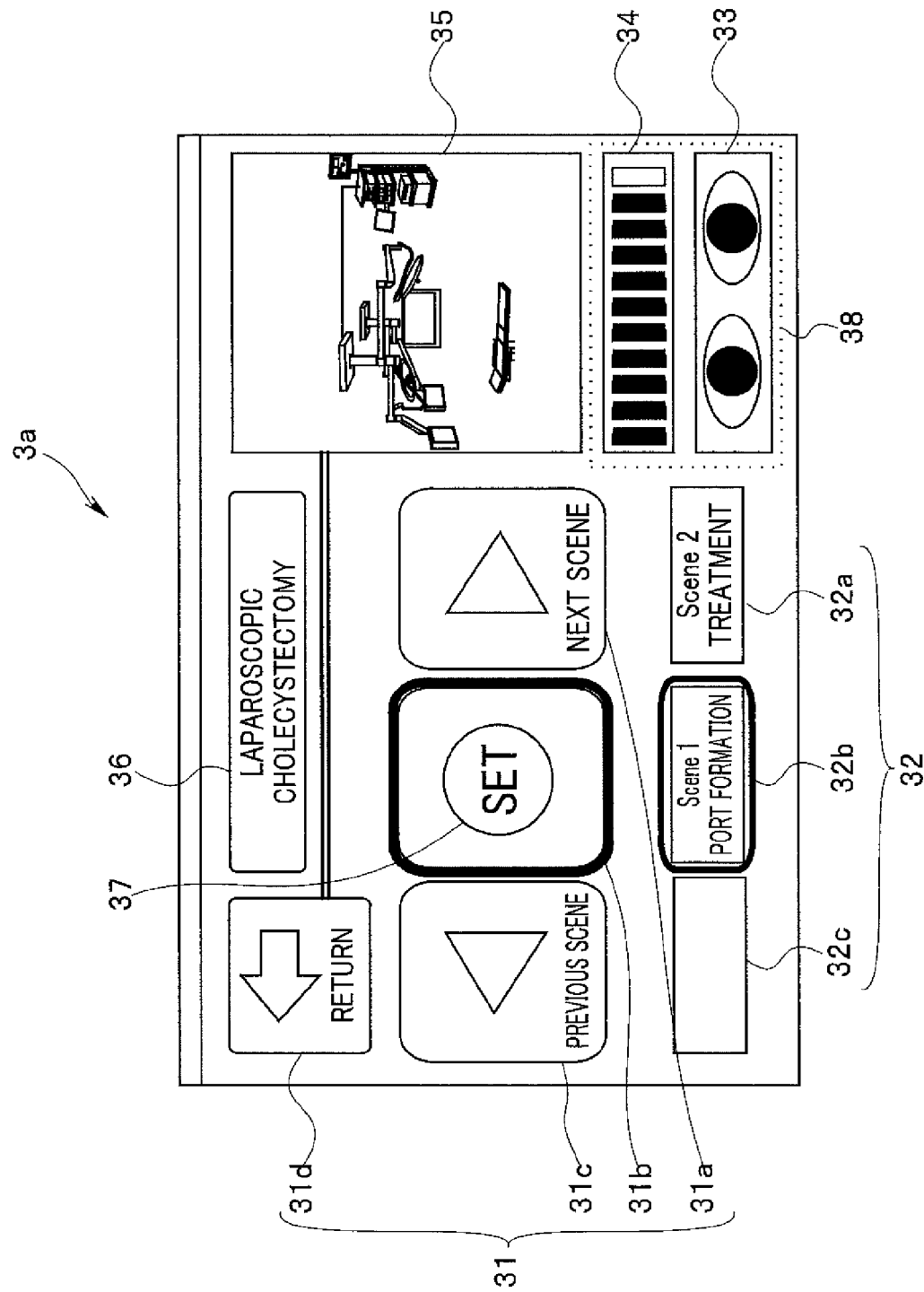

A configuration of the sight line operation screen 3*a* will be described with use of FIG. 5. FIG. 5 is a view explaining an example of the sight line operation screen 3*a*. As shown in FIG. 5, in the sight line operation screen 3*a*, command areas 31*a*, 31*b*, 31*c* and 31*d* as operation instruction regions which issue commands when the sight line of the surgeon closely observes the regions for a fixed time period, and instruct operations to the peripheral apparatuses 2, and command information display areas 32*a*, 33*b* and 32*c* that display information on operation contents of the command areas 31*a*, 31*b* and 31*c* and the like are disposed. Further, in the sight line operation screen 3*a*, a sight line recognition level display area 38 as a sight line recognition level display section is disposed. The sight line recognition level display area 38 includes an eyeball recognition situation display area 33 as an eyeball recognition situation display section that displays an eyeball measurement situation of the surgeon, and a sight line measurement level display area 34 as a sight line measurement level display section that displays a sight line measurement situation of the surgeon.

Further, in the sight line operation screen 3*a*, an apparatus situation display area 35 that displays situations (present set states) of the peripheral apparatuses 2 operable by sight line recognition, and a surgical operation information display area 36 that displays information on a surgical operation that is performed at present, such as a name of the surgical operation are also disposed.

The command areas 31*a* to 31*d* are configured so that when the sight line of the surgeon closely observes insides of the respective areas continuously for a fixed time period, commands that are set in advance according to the respective areas are issued, and a plurality of peripheral apparatuses 2 can be set and changed collectively. When a specific command area is selected by the surgeon closely observing the specific command area, a measurement time period display section (hereinafter, referred to as a timer display) 37 that expresses a continuous close observation time period is displayed by being superimposed on the command area. Specific configurations of the respective command areas 31*a* to 31*d* will be explained with use of an example of a case where in a surgical operation that executes a plurality of scenes in a fixed sequence, the peripheral apparatuses 2 need to be collectively set at a time of start of the respective scenes being cited as an example.

As shown in FIG. 5, the command areas 31*a*, 31*c* and 31*d* are configured for selection of a scene in which an operation is performed (for example, the command area 31*a* is for shifting to a scene which is executed next to a scene selected at present, the command area 31*c* is for shift to a scene that is executed directly before the scene selected at present, and the command area 31*d* is for shift to a first scene). Further, the command area 31*b* is configured to be for collective setting of the peripheral apparatuses 2 at the time of start of the scene selected at present.

Note that the command information display areas 32*a*, 32*b* and 32*c* are respectively brought into one-to-one correspondence with the command areas 31*a*, 31*b* and 31*c*. More specifically, in the command information display area 32*b*, information expressing the scene which is selected at present, such as "Scene 1 (PORT FORMATION)" is displayed, and in the command information display area 32*a*, information expressing a scene which is executed next to the scene selected at present such as "Scene 2 (TREATMENT)" is displayed. Note that display is not specially performed with respect to the command information display area 32 corresponding to the command area 31 which is unable to be selected, for the reason that the scene selected at present is the first scene of a surgical operation, and a scene executed before the first scene is not present, or the like. (For example, the command information display area 32*c* in FIG. 5.)

In this way, the area which issues a command to operate setting of the peripheral apparatuses 2 is configured to be limited only to the command area 31*b*, whereby even when the command areas 31*a*, 31*c* and 31*d* are unintentionally observed closely, the command to instruct operations of the peripheral apparatuses 2 is not issued, and therefore, erroneous operations of the peripheral apparatuses 2 can be prevented.

Note that the command areas 31*a* to 31*d* are not limited to the aforementioned configuration, but the respective command areas 31*a* to 31*d* and operations of the peripheral apparatuses 2 in the respective scenes may be brought into one-to-one correspondence, for example. For example, the command areas 31*a* to 31*d* may be configured such that the command area 31*a* is for collective setting of the peripheral apparatuses 2 at a time of start of the scene 1 (port formation), and the command area 31*b* is for collective setting of the peripheral apparatuses 2 at the time of start of the scene 2 (treatment). Further, the number of command areas 31 which are disposed on the sight line operation screen 3*a* is not limited to four, but a necessary number of command areas 31 can be disposed.

In the eyeball recognition situation display area 33, the determination result in the eyeball measurement level determination section 22 is displayed. FIG. 6 is a view showing an example of display contents of the eyeball recognition situation display area 33. When the position coordinates of both eyes of a surgeon are measured in the sight line measuring apparatus 15, an image showing a state where both eyes are opened as shown in an uppermost tier in FIG. 6, for example, is displayed in the eyeball recognition situation display area 33. Further, when position coordinates of a left eye of an operator are not measured though position coordinates of a right eye of the operator are measured, an image showing a state where a left eye is closed while a right eye opens as shown in a second tier from a top in FIG. 6, for example, as a mirror image is displayed in the eyeball recognition situation display area 33. Further, when the position coordinates of the right eye of the surgeon are not measured although the position coordinates of the left eye of the surgeon are measured, an image showing a state where the right eye is closed while the left eye opens as shown in a third tier from the top in FIG. 6, for example, as a mirror image is displayed in the eyeball recognition situation display area 33. Further, when the position coordinates of the right eye and the left eye are not measured, an image showing a state where both the eyes are closed as shown in a lowermost tier in FIG. 6, for example, is displayed in the eyeball recognition situation display area 33.

It can sometimes happen that although a surgeon intends to observe the specific command area 31 closely with both eyes, a sight line of one eye or sight lines of both eyes is or are not recognized, because the surgeon closes his or her eyes partly, often blinks, or the sight lines are out of the measurement enabling region of the sight line measuring apparatus 15 because a face orientation or a body position is improper. Therefore, in the present embodiment, the recognition situation of the sight line is displayed on the sight line operation screen 3*a* to be visually understandable, whereby the surgeon can grasp whether or not the sight lines of both eyes of himself or herself are reliably recognized in real time. Accordingly, when the surgeon cannot perform a sight line operation against the intention of the surgeon, the surgeon can grasp the cause relatively easily, and can concentrate on an operation without stress.

Note that when only either one of a right eye or a left eye is recognized, a sight line operation can be performed, but the operation is highly likely to be disabled as compared with a case where both the eyes are recognized. Accordingly, as a result that the state where only one eye is recognized is displayed, an effect of urging a surgeon to bring the eye which is not recognized into a recognizable state is obtained, and therefore, the sight line operation can be performed more reliably.

In the sight line measurement level display area 34, the index which is generated in the sight line measurement level calculation section 21 is displayed as a sight line measurement level. The index is displayed in a format of a level meter as shown in FIG. 5, for example. A case where a sight line cannot be measured at all is set as zero, and as the value of the index expressing reliability of sight line measurement becomes larger, a bar extends to a right direction. Note that although the display format of the sight line measurement level in the sight line measurement level display area 34 is not limited to the format shown in FIG. 5, other desired formats can be used, such as display in numerical values, and use of a circle graph display, but a display format which is visually understandable for a surgeon is desirably used.

It can happen that even though a surgeon intends to perform a surgery and an operation with a distance from the sight line operation screen 3*a* kept constant, the surgeon moves his or her face close to the sight line operation screen 3*a* unconsciously, bends his or her head, or changes his or her posture unintentionally. Therefore, in the present embodiment, the sight line measurement level is displayed on the sight line operation screen 3*a* to be visually understandable, whereby a surgeon can grasp to what extent the sight lines of himself or herself are measured reliably in real time. Accordingly, when the surgeon cannot perform a sight line operation against the intention of the surgeon, the surgeon can grasp the cause relatively easily, and can concentrate on an operation without stress.

Note that a sight line operation can be performed even if reliability of measurement of sight lines is low, but it is highly possible that operation is disabled or an erroneous operation is caused due to a slight displacement of a posture. The measurement level is displayed gradually, whereby the effect of urging a surgeon to raise the sight line measurement level can be obtained, before sight line measurement cannot be performed to disable an operation or cause an erroneous operation, and therefore, a sight line operation can be performed more reliably.

The measurement section 24 measures a time period in which sight line position coordinates of a surgeon closely observe a specific command area continuously by a counter or the like. A measurement result of the measurement section 24 is outputted to the GUI generation section 20, and is displayed in a predetermined place on the sight line operation screen 3*a* as the measurement time period display section 37 (hereinafter, referred to as a timer display 37).

Figure 7:
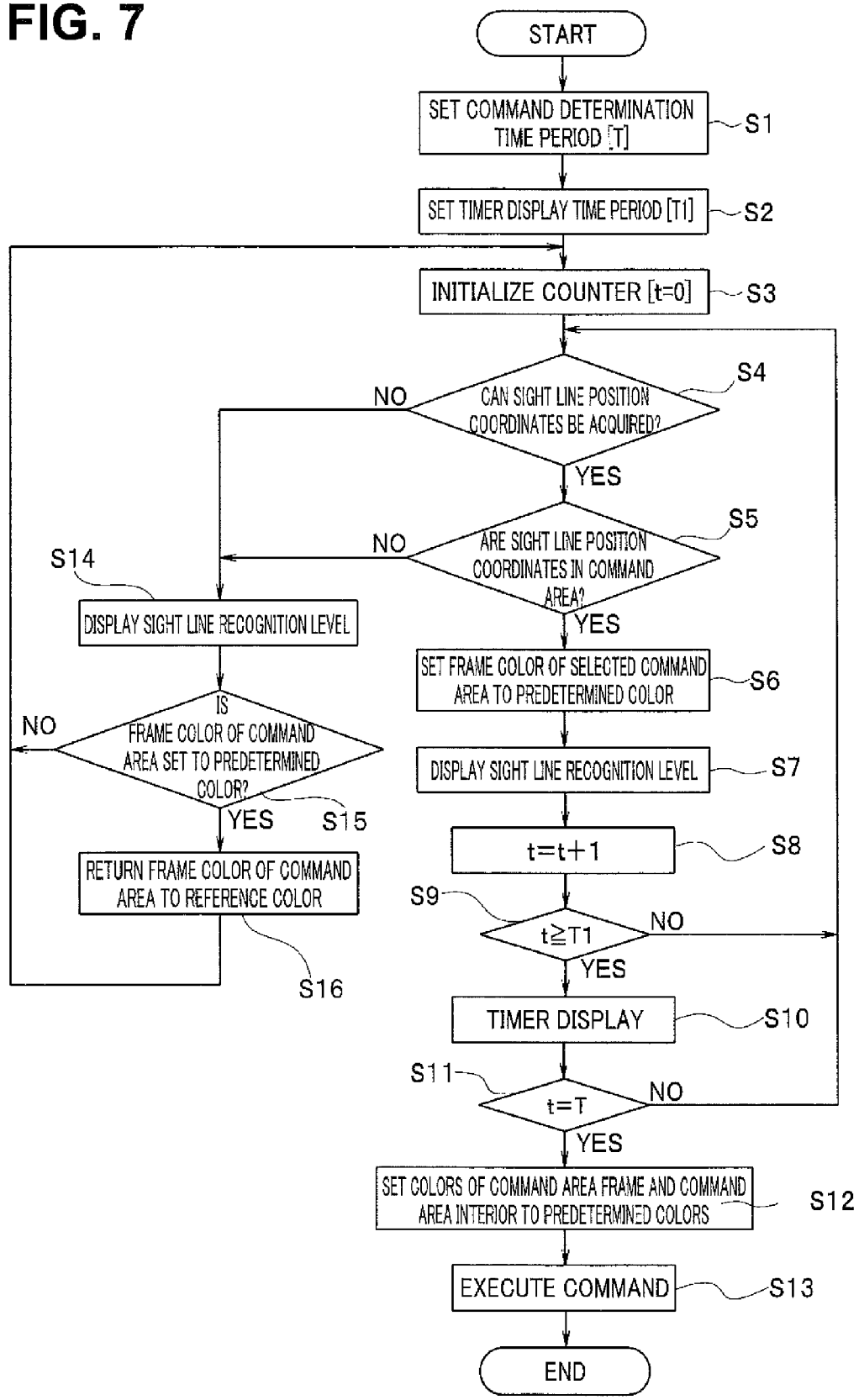
FIG. 7 is a flowchart explaining a series of flows up to a command execution by sight line recognition.

Next, an operation of the medical system 1 in the present embodiment will be described with use of FIG. 7 and FIG. 8. FIG. 7 is a flowchart explaining a flow of processing of command execution by sight line recognition, and FIG. 8 is a diagram explaining an example of timer display that is shown in a selected command area.

First, a time period (hereinafter, referred to as a command determination time period [T]) until a command is issued after sight line coordinates of a surgeon enter the specific command area 31, and start close observation is set (step S1). The command determination time period [T] is set to a sufficient time period for a surgeon to become aware of a mistake and turn away his or her sight lines when the surgeon selects an erroneous command area. However, if the time period is too long, the surgeon needs to continue to observe the command area closely for a substantial time period until a command is issued, and therefore, it is feared that stress is exerted on the surgeon, and the surgeon cannot concentrate on an operation. Therefore, the command determination time period [T] needs to be set to be in a sensible range so as not to be uselessly long, and is desirably set to approximately two to three seconds, for example.

Next, a time period (hereinafter, referred to as a timer display start time period [T1]) until the timer display 37 is started in the command area after the sight line coordinates of the surgeon enter the specific command area, and start close observation is set (step S2). Note that the timer display start time period [T1] needs to be set to a time period shorter than the command determination time period [T]. For example, when the command determination time period [T] is two seconds, the timer display start time period is set to a time period less than two seconds (0.5 second, for example).

Here, the timer display 37 that counts the close observation time period in the specific command area will be described with use of FIG. 8. As for the timer, a display method can be used, such that an area of a fan shape increases in association with the time period in which the specific command area is closely observed continuously, and the area becomes a true circle when the close observation time period reaches the command determination time period. The timer is displayed in the command area which is selected by sight line recognition when a time period reaches the timer display start time period [T1] which is set in the present step.

Note that the display method of the timer is not limited to the display method illustrated in FIG. 8, but various display methods can be used such as level bar display displayed in the sight line measurement level display area 34, and display of a sandglass type. Further, although the display method illustrated in FIG. 8 uses a count-up method that increases the area of the fan shape with the close observation time period, a countdown method may be used, which decreases the area of the fan shape so that display disappears (or only an outer circumference of the circle is displayed) when the close observation time period reaches the command determination time period. Note that in the case of using any display method, the timer is desirably displayed transparently so as not to hide the display content in the selected command area.

If the timer display 37 is continuously changing on the sight line operation screen 3a, it may happen that a surgeon is bothered by the timer display 37 so much that the surgeon cannot concentrate on an operation. Therefore, as shown in FIG. 8, for example, display may be switched to a fan shape corresponding to each of time periods when the time period in which the inside of the specific command area is continuously observed closely reaches set time periods (0.5 second, 0.67 second, 0.83 second, 1 second, 1.17 seconds, 1.33 seconds, 1.5 seconds and 1.83 seconds) after the timer display start time period [T1]. That is, in an example shown in FIG. 8, display is changed nine times after the command area is selected and measurement of a close observation time period is started.

The timer display 37 is made in the selected command area in this way, whereby a surgeon can visually grasp a residual time period until command determination easily, and therefore the surgeon can concentrate on an operation without feeling uneasy about a wait time period until command determination, or feeling stress.

Subsequently, zero is set to a counter [t] that measures the time period in which the surgeon closely observes the inside of the specific command area 31, so that the counter is initialized (step S3).

Subsequently, the position coordinates of the sight lines of the surgeon are measured by the sight line measuring apparatus 15. When the sight line position coordinates of at least one eye of the surgeon can be measured (step S4, YES), the flow proceeds to step S5, and the position coordinates of sight line, which are acquired, and internal position coordinates of the command areas 31a, 31b, 31c and 31d which are disposed on the sight line operation screen 3a are compared. When the position coordinates of the sight line are present in the internal coordinates of any one area of the command areas 31a, 31b, 31c and 31d (step S5, YES), in order to make it clear that the command area (for example, the command area 31b) where the position coordinates of the sight line are present in the internal region is selected as a target of the sight line operation, a frame color of the command area 31b is changed to a color (for example, a yellow color) that is different from a color of the command areas 31a, 31c and 31d which are not selected (step S6).

Note that since an object of the present step is to perform highlighting so that the surgeon can easily recognize that the command area 31b is selected, changes such as changing thickness of the outer frame (thickening), changing a color of an interior of the command area 31b may be performed, instead of changing the frame color, and a plurality of these changes may be performed in combination. Further, in the present step, the command information display area 32b which is in one-to-one correspondence with the selected command area 31b may be highlighted by change of a frame color, change of thickness of the frame or the like.

As shown in FIG. 5, for example, the outer frame of the selected command area 31b and the outer frame of the command information display area 32b which is in correspondence with the command area 31b are made thicker than outer frames of the other command areas 31a, 31c and 31d and command information display areas 32a and 32c, whereby the selected command area 31b may be highlighted.

When the position coordinates of neither of the sight lines of both the eyes of the surgeon can be measured (step S4, NO), or when the position coordinates of the sight line of the surgeon are not included in the internal region of any of the command areas 31a, 31b, 31c and 31d (step S5, NO), a present sight line recognition level is displayed (step S14), and it is confirmed whether or not a command area that is highlighted by the frame color being changed or the like is present (step S15). If the highlighted command area is present (step S15, YES), highlighting is canceled by the frame color being returned to the same reference color as the other command areas or the like (step S16), and the flow returns to initialization of the counter (step S3).

Note that the sight line recognition level displayed in step S14 includes both the eyeball recognition situation which is displayed in the eyeball recognition situation display area 33, and the sight line recognition level which is displayed in the sight line measurement level display area 34. Accordingly, when the position coordinates of the sight lines of both the eyes of the surgeon cannot be measured (step S4, NO), the display content shown in the lowest tier in FIG. 6 is displayed in the eyeball recognition situation display area 33, and display showing that the sight line recognition level is zero is made in the sight line measurement level display area 34, in the present step. When the position coordinates of the sight line of the surgeon is not included in the internal region of any of the command areas 31a, 31b, 31c and 31d (step S5, NO), display corresponding to the eyeball recognition situation at the point of time is made in the eyeball recognition situation display area 33, and display showing the sight line recognition level at the point of time is made in the sight line measurement level display area 34.

When highlighting processing of the selected command area 31b is ended in step S6, a present sight line recognition level is displayed (step S7), and the counter is incremented (step S8). When the counter does not reach the timer display start time period, that is, t<T1 (step S9, NO), the flow returns to measurement of the position coordinates of the sight line of the surgeon by the sight line measuring apparatus 15 (step S4).

Note that the sight line recognition level displayed in step S7 also includes both of the eyeball recognition situation displayed in the eyeball recognition situation display area 33, and the sight line recognition level displayed in the sight line measurement level display area 34, similarly to step S14.

When the counter reaches the timer display start time period, that is, t≥T1 (step S9, YES), the timer display 37 as shown in FIG. 8 is made in the selected command area 31b (step S10). When the counter does not reach the command determination time period, that is, t<T (step S11, NO), the flow returns to measurement of the position coordinates of the sight line of the surgeon by the sight line measuring apparatus 15 (step S4).

When the counter reaches the command determination time period (t=T) (step S11, YES), the frame color and the color of an inside of the frame of the selected command area 31b are changed. The frame color is changed to a color (for example, a red color) that is different from the frame color (the reference color) of the other command areas 31a, 31c and 31d which are not selected, and a color (for example, a yellow color) which is set as the frame color of the command area 31b so far. Further, the color of the inside of the frame is changed to a color (for example, a light blue color) that is a color which is different from a color of insides of frames of the other command areas 31a, 31c and 31d which are not selected and a color that is set as the color of the inside of the frame of the command area 31b so far, and is a color (a light blue color, for example) that does not make the display in the command area difficult to read.

Note that since an object of the present step is to perform highlighting so that the surgeon can easily recognize that the command set to the command area 31b is executed, the thickness of the outer frame of the command area 31b may be changed (thickened). Further, means that is recognizable by auditory sense other than sense of vision, such as making a beep sound may be used in combination. Further, in the present step, the command information display area 32b which is in one-to-one correspondence with the selected command area 31b may be highlighted by the frame color being changed, a thickness of the frame being changed or the like.

In the end, the command which is set to the command area 31b is executed (step S13), and the series of processing shown in FIG. 7 is ended.

In this way, according to the present embodiment, the eyeball recognition situation display area 33 and the sight line measurement level display area 34, which display the sight line recognition level, are provided on the sight line operation screen 3a. The eyeball recognition situation is displayed in the eyeball recognition situation display area 33, and the sight line recognition level is displayed in the sight line measurement level display area 34. Accordingly, even when the sight line is not recognized, a surgeon can easily grasp the cause of the sight line being not recognized, by referring to the displays in the eyeball recognition situation display area 33 and the sight line measurement level display area 34, and therefore, the surgeon can concentrate on an operation without feeling stress.

The respective "sections" in the present description are conceptual matters corresponding to the respective functions of the embodiment, and are not always in one-to-one correspondence with specific hardware and software routines. Accordingly, in the present description, the embodiment is explained with virtual circuit blocks (sections) having the respective functions of the embodiment being assumed. Further, the respective steps of the respective procedures in the present embodiment may be executed in such a manner that an execution sequence is changed, a plurality of steps are simultaneously executed, or the respective steps are executed in a different sequence at each execution, as long as the execution is not against the characteristics of the respective steps. Furthermore, all or some of the respective steps of the respective procedures in the present embodiment may be realized by hardware.

Although embodiments of the present invention are explained, the embodiments are illustrated as examples, and do not intend to restrict the scope of the invention. The novel embodiments can be carried out in other various modes, and various omissions, replacements and modifications can be made within the range without departing from the gist of the present invention. The embodiments and modification of the embodiments are included in the scope and the gist of the invention, and also included in the invention described in the claims and an equivalent range of the invention.

According to the medical system of the present invention, in the case where the sight line is not recognized, a surgeon can easily grasp the cause, and the surgeon can concentrate on an operation.

What is claimed is:

1. A medical system, comprising:
   a plurality of controlled apparatuses;
   a display section in which an operation instruction region for instructing operation of the controlled apparatuses is displayed;
   a sight line detection section configured to detect sight line position coordinates of an operator who performs operation of the controlled apparatuses via the display section;
   a sight line measurement level calculation section configured to calculate an index showing reliability of the sight line position coordinates which are detected by the sight line detection section; and
   a sight line recognition level calculation section configured to calculate an extent of sight line recognition of the operator from a calculation result of the sight line measurement level calculation section,
   wherein the sight line recognition level calculation section has an eyeball measurement level determination section configured to determine whether or not the respective sight line position coordinates of a left eye and a right eye of the operator are detected in the sight line detection section, independently respectively.

2. The medical system according to claim 1, comprising:
   a sight line recognition level display section configured to display a calculation result of the sight line recognition level calculation section on the display section.

3. The medical system according to claim 2,
   wherein the sight line recognition level display section has an eyeball recognition situation display section configured to display a determination result by the eyeball measurement level determination section, and a sight line measurement level display section configured to display a calculation result by the sight line measurement level calculation section.

4. The medical system according to claim 3,
   wherein the eyeball recognition situation display section displays the determination result of the left eye and the determination result of the right eye independently respectively.

5. The medical system according to claim 3,
wherein the sight line measurement level display section displays the index in a format of a level meter.

6. The medical system according to claim 1,
wherein the sight line measurement level calculation section calculates the index by using a distance between the sight line detection section and the operator.

7. The medical system according to claim 1,
wherein the sight line measurement level calculation section calculates the index by using level information of the sight line position coordinates outputted from the sight line detection section.

8. The medical system according to claim 1, further comprising:
a measurement section configured to measure a time period in which the sight line position coordinates are continuously present in the operator instruction region; a measurement time period display section configured to display a measurement time period of the measurement section by superimposing the measurement time period on the operation instruction region; and a control section configured to control operation of the controlled apparatuses when the measurement time period exceeds a predetermined time period.

9. The medical system according to claim 8,
wherein the measurement time period display section is a timer display that changes in time series.

10. The medical system according to claim 8,
wherein display in the operation instruction region is identifiable transparently through the measurement time period display section.

* * * * *